US006488695B1

(12) United States Patent
Hickingbotham

(10) Patent No.: US 6,488,695 B1
(45) Date of Patent: Dec. 3, 2002

(54) OPHTHALMOLOGIC SURGICAL PROBE

(75) Inventor: Dyson W. Hickingbotham, Stouchsburg, PA (US)

(73) Assignee: Alcon, Inc., Hunenberg (CH)

( * ) Notice: Subject to any disclaimer, the term of this patent is extended or adjusted under 35 U.S.C. 154(b) by 223 days.

(21) Appl. No.: 09/641,066

(22) Filed: Aug. 17, 2000

(51) Int. Cl.[7] ............................................. A61B 17/28
(52) U.S. Cl. ..................................................... 606/206
(58) Field of Search .............................. 606/206, 166, 606/174, 169, 170, 171, 13

(56) References Cited

U.S. PATENT DOCUMENTS

| | | | |
|---|---|---|---|
| 4,201,213 A | 5/1980 | Townsend | |
| 4,258,716 A | 3/1981 | Sutherland | |
| 4,433,687 A | * 2/1984 | Burke et al. | ................ 128/318 |
| 4,877,026 A | 10/1989 | de Laforcade | |
| 5,263,958 A | 11/1993 | deGuillebon et al. | |
| 5,275,607 A | 1/1994 | Lo et al. | |
| 5,290,302 A | 3/1994 | Pericic | |
| 5,350,391 A | 9/1994 | Iacovelli | |
| 5,355,871 A | * 10/1994 | Hurley | .......................... 128/20 |
| 5,395,386 A | 3/1995 | Slater | |
| 5,443,476 A | 8/1995 | Shapiro | |
| 5,562,693 A | 10/1996 | Devlin et al. | |
| 5,562,699 A | * 10/1996 | Heimberger | ................. 606/205 |
| 5,634,918 A | 6/1997 | Richards | |
| 5,695,521 A | * 12/1997 | Anderhub | ..................... 606/205 |
| 5,897,507 A | * 4/1999 | Kortenbach et al. | ......... 600/562 |

FOREIGN PATENT DOCUMENTS

DE      35 26 821 A1      10/2001

OTHER PUBLICATIONS

Alcon® Vision Care Brochure Providing Product Information for New Tears Naturale™ Punctal Plugs, 1278 OPP (1998).
Grieshaber Switzerland Brochure Providing Product Information for The Grieshaber Sutherland Round Handle (02.97).
Grieshaber Switzerland Brochure Providing Product Information for The Grieshaber Foreign Body Forceps (03.99).

* cited by examiner

*Primary Examiner*—Peter Nerbun
*Assistant Examiner*—Katerine Moran
(74) *Attorney, Agent, or Firm*—Jeffrey S. Schira

(57) ABSTRACT

A probe having an actuation handle made from springy material having a memory. Squeezing the handle causing the actuation device to elongate, thereby causing movement in the probe tip. The probe handle of the present invention may be held and actuated in any position.

5 Claims, 5 Drawing Sheets

OPHTHALMOLOGIC SURGICAL PROBE

BACKGROUND OF THE INVENTION

This invention relates generally to the field of surgical probes and, more particularly, to ophthalmologic surgical probes.

During ophthalmologic microsurgery, it is often necessary to dissect, cut, delaminate or otherwise manipulate delicate tissues within the eye. Microsurgical tools, such as microscissors, micro forceps and other devices generally are used for such manipulations. Many of these devices require some sort of actuation (i.e., the blades of a scissors must be rotated across each other in order to cut, the grasping tips of a forceps must be bought together in order to grasp, etc.).

Many prior art devices use plunger-like devices actuated by a finger operated levers (U.S. Pat. No. 4,258,716 (Sutherland)). Other prior art devices use a handle that is squeezed to operate the probe tip (U.S. Pat. No. 4,433,687 (Burke, et al.)).

These prior art devices all require a relatively expensive drive mechanism, making the cost of these devices prohibitive for a single-use, disposable device.

Therefore, a need continues to exist for a simple, inexpensive actuator handle for microsurgical probes.

BRIEF SUMMARY OF THE INVENTION

The present invention improves upon the prior art by providing a probe having an actuation handle made from springy material having a memory. Squeezing the handle causes the actuation device to elongate, thereby causing movement in the probe tip. The probe handle of the present invention may be held and actuated in any position.

Accordingly, one objective of the present invention is to provide a simple probe actuation handle.

Another objective of the present invention is to provide an inexpensive probe actuation handle.

Still another objective of the present invention is to provide a probe actuation handle that may be held and actuated in any position.

These and other advantages and objectives of the present invention will become apparent from the detailed description and claims that follow.

DETAILED DESCRIPTION OF THE INVENTION

Figure 1:
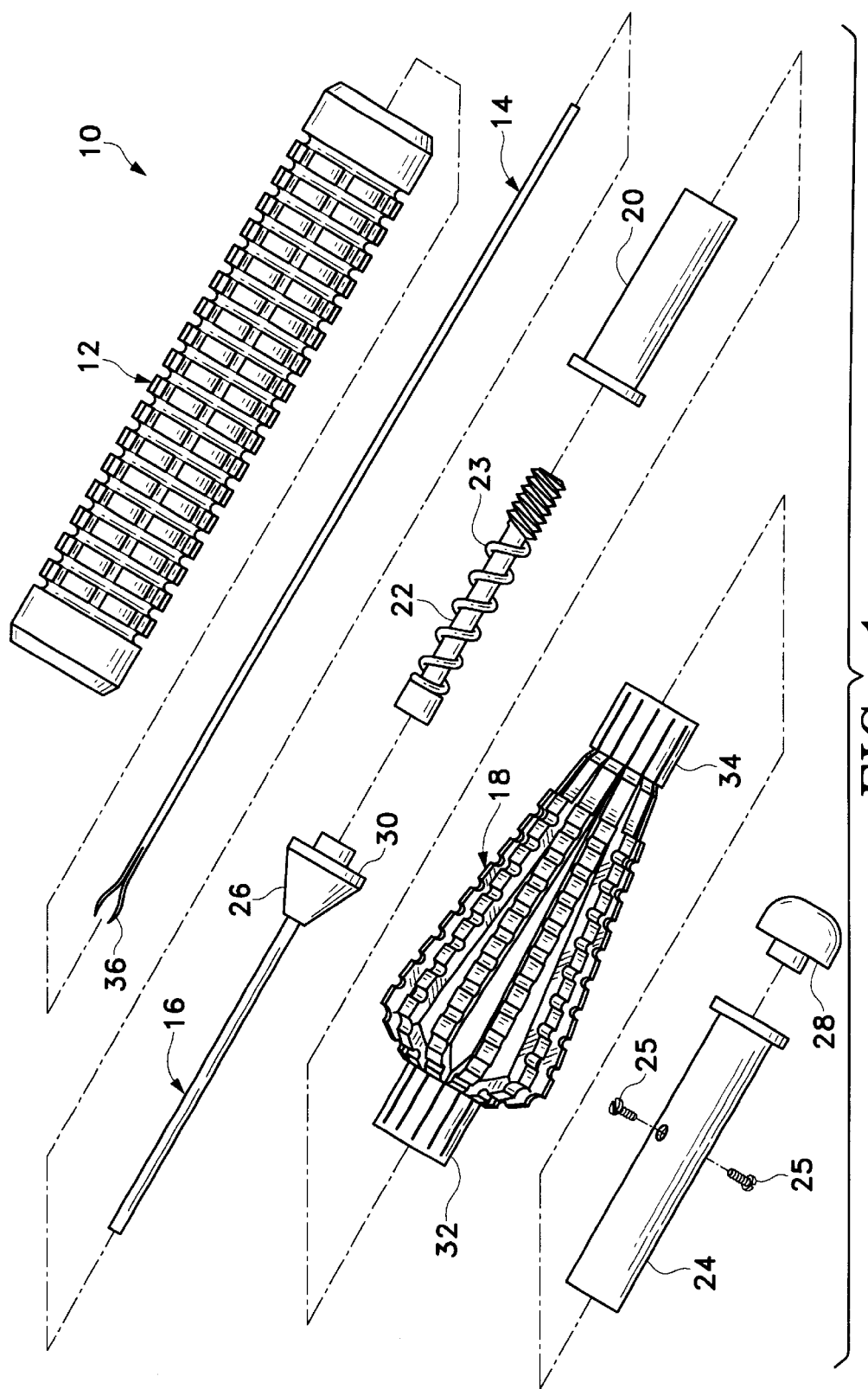
FIG. 1 is an exploded perspective view of one embodiment of the probe of the present invention.

As best seen in 1, probe 10 generally consists of handle extension 12, probe tip 14, probe tip actuation tube 16 and probe actuation handle 18. Handle extension 12 may be made of any suitable material such as injection molded or machined thermoplastic or metal and may be textured or knurled to improve gripping of extension 12. Probe tip 14 may be any suitable type of manipulation device, such as forceps or scissors and will generally be made from stainless steel or titanium, but other materials may also be used. Tube 16 may be any suitable medical grade tubing, such as titanium, stainless steel or plastic and is sized so that probe tip 14 reciprocates easily within tube 16. Actuation handle 18 may be made from any suitable springy material having a memory, such as titanium, stainless steel or suitable thermoplastic.

Figure 2:
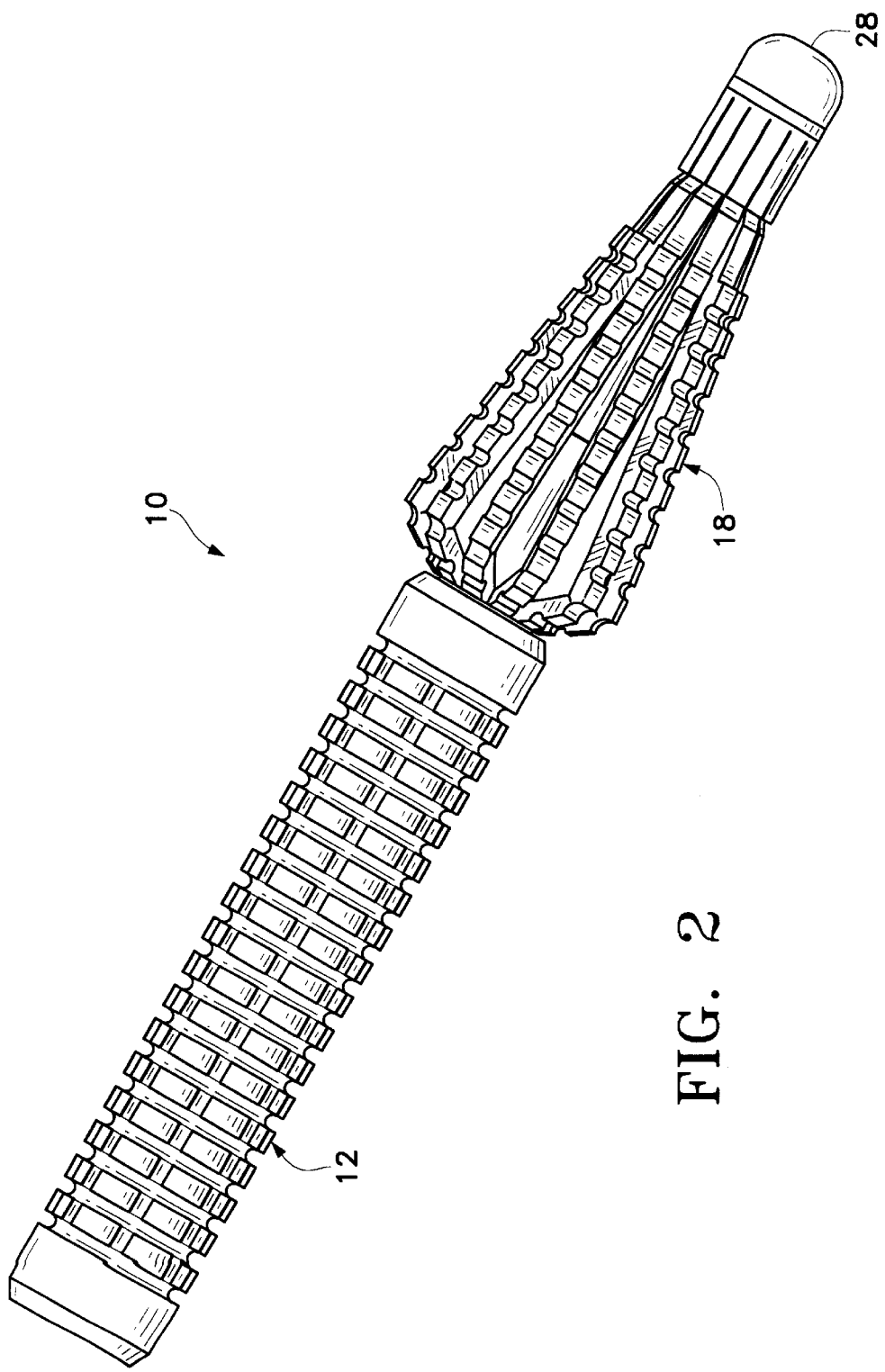
FIG. 2 is a perspective view of the embodiment of the probe shown in FIG. 1 with the probe handle extension piece covering the probe tip.
Figure 3:
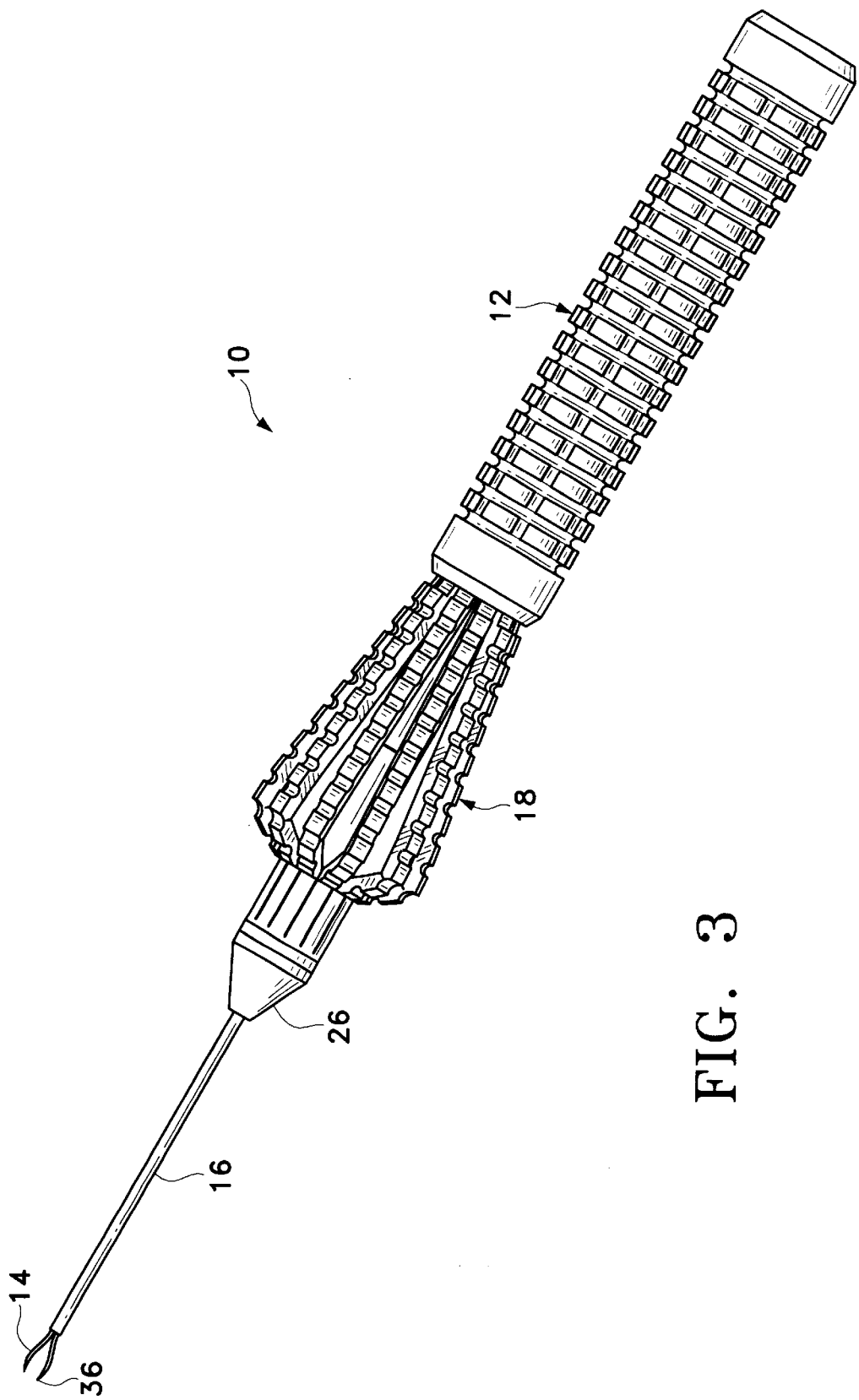
FIG. 3 is a perspective view of one embodiment of the probe of the present invention similar to FIG. 2 except with the probe handle extension piece is assembled on the probe handle and the probe tip is uncovered.
Figure 5:
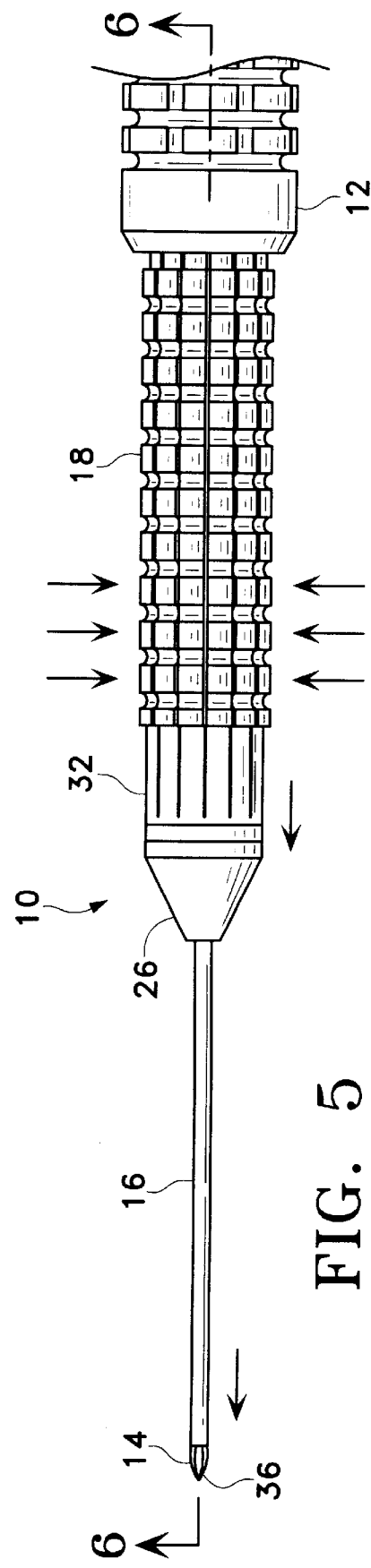
FIG. 5 is a top plan view of one embodiment of the probe of the present invention shown in its compressed state.
Figure 6:
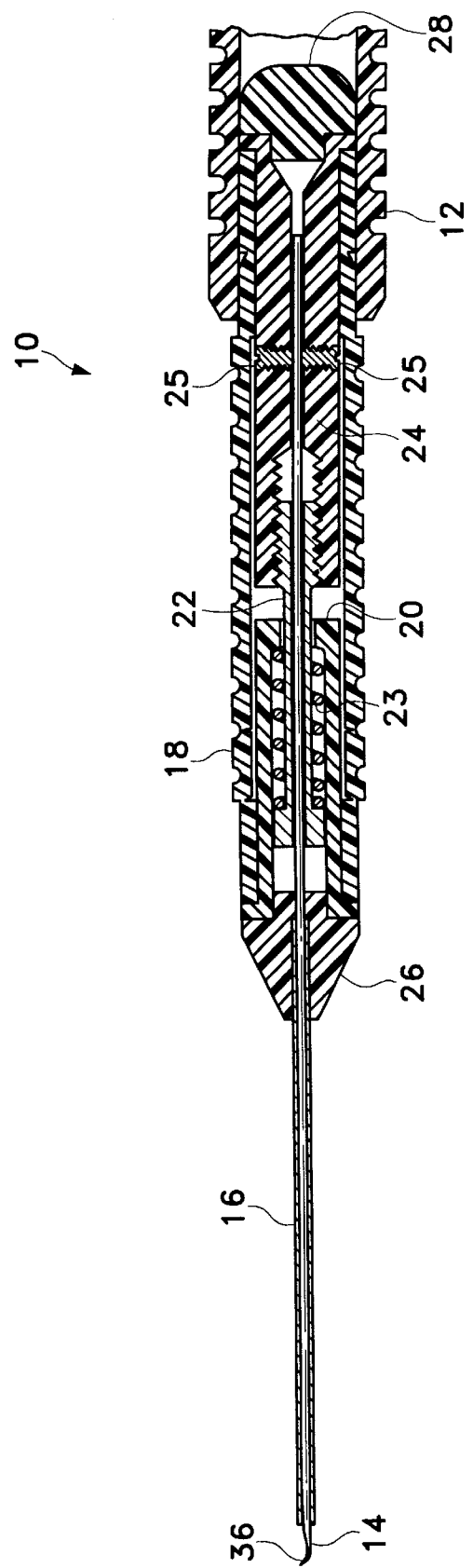
FIG. 6 is a cross-sectional view of one embodiment of the probe of the present invention shown in its compressed state.

As best seen in FIGS. 1 and 6, probe 10 is assembled by placing adjustment screw 22 with return spring 23 attached first through actuation sleeve 20 and then through handle 18 and screwing screw 22 into end sleeve 24. Nose cone 26 on tube 16 is inserted into and affixed to actuation sleeve 20. End cap 28 is pressed into end sleeve 24. Probe tip 14 is then slid within the tube/sleeve assembly and held in place by setscrews 25. Setscrews 25 allow for precise alignment of tube 16 during assembly and return spring 23 returns tube 16 to its original position following actuation. Handle extension 12 may be frictionally fit over front portion 32 on actuation handle 18, so as to protect tip 14 (as best seen in FIG. 2), or over rear portion 34 on actuation handle 18, so as to provide an extension to actuation handle 18 (as best seen in FIGS. 3-6).

Figure 4:
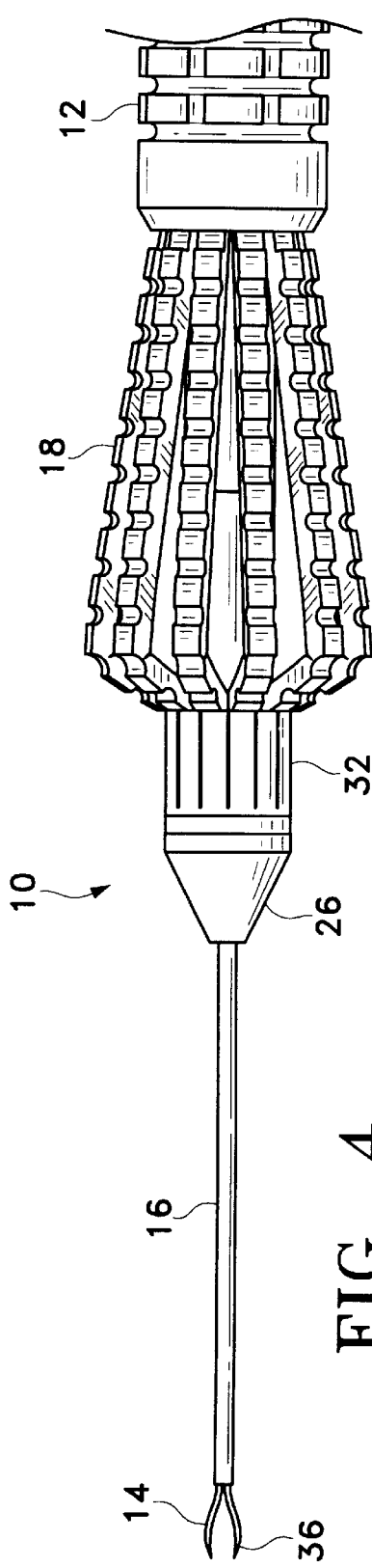
FIG. 4 is a top plan view of one embodiment of the probe of the present invention shown in its relaxed state.

As best seen in FIGS. 4 and 5, in use, when actuation handle 18 is in its relaxed stated, distal end 36 of tip 14 protrudes a relatively large amount from tube 16. Squeezing of actuation handle 18 (as seen in FIG. 5) forces front portion 32 of actuation handle 18 forward, because rearward movement of rear portion 34 of actuation handle 18 is prevented by end sleeve 24. The forward movement of front portion 32 of actuation handle 18 is transferred to tube 16 through rim 30 on nose cone 26, causing tube 16 to slide forward over distal end 36 of probe tip 14, thereby compressing together distal end 36. The amount of movement of tube 16 over distal tip 36 can be controlled easily by varying the outer diameter of actuation handle 18 in its relaxed stated, with larger diameters causing greater longitudinal movement.

This description is given for purposes of illustration and explanation. It will be apparent to those skilled in the relevant art that changes and modifications may be made to the invention described above without departing from its scope or spirit.

I claim:

1. A probe, comprising:
   a) an actuation handle having a first diameter and a first length in its relaxed state and a second diameter and a second length in its compressed state, the first diameter being larger than the second diameter and the second length being longer than the first length;
   b) an actuation sleeve fixed to the distal end of the actuation handle;
   c) an end sleeve fixed to the proximal end of the actuation sleeve;
   d) a nose cone having an actuation tube received on the distal end of the actuation sleeve; and
   e) a probe tip telescopically received through the actuation tube and the actuation sleeve and fixed to the end sleeve so that compression of the actuation handle causes the actuation tube to reciprocate over the probe tip.

2. The probe of claim 1 further comprising an adjusting screw received in the end sleeve and a return spring received on the adjusting screw.

3. The probe of claim 1 wherein probe tip is a forceps.

4. The probe of claim 1 further comprising an actuation handle extension capable of alternatively extending the length of the actuation handle or covering the actuation tube and probe tip.

5. A probe, comprising:
- a) an actuation handle having a first diameter and a first length in its relaxed state and a second diameter and a second length in its compressed state, the first diameter being larger than the second diameter and the second length being longer than the first length;
- b) an actuation sleeve fixed to the distal end of the actuation handle;
- c) an end sleeve fixed to the proximal end of the actuation sleeve;
- d) a nose cone having an actuation tube received on the distal end of the actuation sleeve; and
- e) a probe tip having a forceps telescopically received through the actuation tube and the actuation sleeve and fixed to the end sleeve so that compression of the actuation handle causes compression of the forceps.

\* \* \* \* \*